(12) United States Patent
Hoong Sim et al.

(10) Patent No.: US 9,532,742 B2
(45) Date of Patent: Jan. 3, 2017

(54) SYRINGE WITH BREAKABLE PLUNGER FOR ARTERIAL BLOOD GAS SAMPLE COLLECTION

(71) Applicant: Becton, Dickinson and Company, Franklin Lakes, NJ (US)

(72) Inventors: Lee Hoong Sim, Singapore (SG); Lim Kiang Heng, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 225 days.

(21) Appl. No.: 14/350,992

(22) PCT Filed: Oct. 18, 2012

(86) PCT No.: PCT/US2012/060790
§ 371 (c)(1),
(2) Date: Apr. 10, 2014

(87) PCT Pub. No.: WO2013/059438
PCT Pub. Date: Apr. 25, 2013

(65) Prior Publication Data
US 2014/0309552 A1    Oct. 16, 2014

Related U.S. Application Data

(60) Provisional application No. 61/549,550, filed on Oct. 20, 2011.

(51) Int. Cl.
*A61B 5/00* (2006.01)
*A61B 5/15* (2006.01)
(Continued)

(52) U.S. Cl.
CPC ........... *A61B 5/15003* (2013.01); *A61B 5/153* (2013.01); *A61B 5/150236* (2013.01);
(Continued)

(58) Field of Classification Search
CPC . A61B 5/1405; A61M 5/3129; A61M 5/3135; A61M 5/31501; A61M 5/31505; A61M 5/31511
See application file for complete search history.

(56) References Cited

U.S. PATENT DOCUMENTS 4,159,713 A    7/1979 Prais
4,821,738 A    4/1989 Iwasaki et al.
(Continued)

FOREIGN PATENT DOCUMENTS

JP            61113431 A      5/1986

*Primary Examiner* — Max Hindenburg
(74) *Attorney, Agent, or Firm* — The Webb Law Firm

(57) ABSTRACT

A fluid collection assembly and method for use thereof is provided including a barrel with a plunger rod slidably inserted is disclosed. The assembly and method are particularly useful in the collection of arterial blood. The plunger rod includes a proximal portion, a distal portion with a stopper, and a breakable connector between the proximal and distal portions. In use, the assembly is primed with a liquid anticoagulant, the breakable connection is broken, and a fluid sample is collected with the arterial pressure causing the distal portion of the plunger rod to travel in a proximal direction along the barrel and contact an annular flange extending within the barrel. After collection, a tip cap can be applied to the assembly to prevent any spillage of the fluid sample during handling, storage, and transportation.

10 Claims, 7 Drawing Sheets

(51) Int. Cl.
*A61M 5/315* (2006.01)
*A61B 5/153* (2006.01)

(52) U.S. Cl.
CPC .. *A61B 5/150244* (2013.01); *A61B 5/150259* (2013.01); *A61B 5/150389* (2013.01); *A61B 5/150503* (2013.01); *A61B 5/150732* (2013.01); *A61B 5/150755* (2013.01); *A61B 5/150908* (2013.01); *A61M 5/31501* (2013.01); *A61M 5/31511* (2013.01)

(56) References Cited

U.S. PATENT DOCUMENTS

| | | |
|---|---|---|
| 5,314,416 A | 5/1994 | Lewis et al. |
| 5,377,689 A | 1/1995 | Mercereau |
| 5,529,738 A | 6/1996 | Mercereau |
| 6,217,550 B1 | 4/2001 | Capes |
| 7,798,993 B2 | 9/2010 | Lim et al. |
| 2003/0181825 A1 | 9/2003 | Büttner |
| 2004/0064105 A1 | 4/2004 | Capes et al. |
| 2004/0176722 A1 | 9/2004 | Capes et al. |
| 2006/0178625 A1 | 8/2006 | Lim et al. |
| 2006/0195063 A1 | 8/2006 | Lim et al. |
| 2008/0097242 A1 | 4/2008 | Cai |

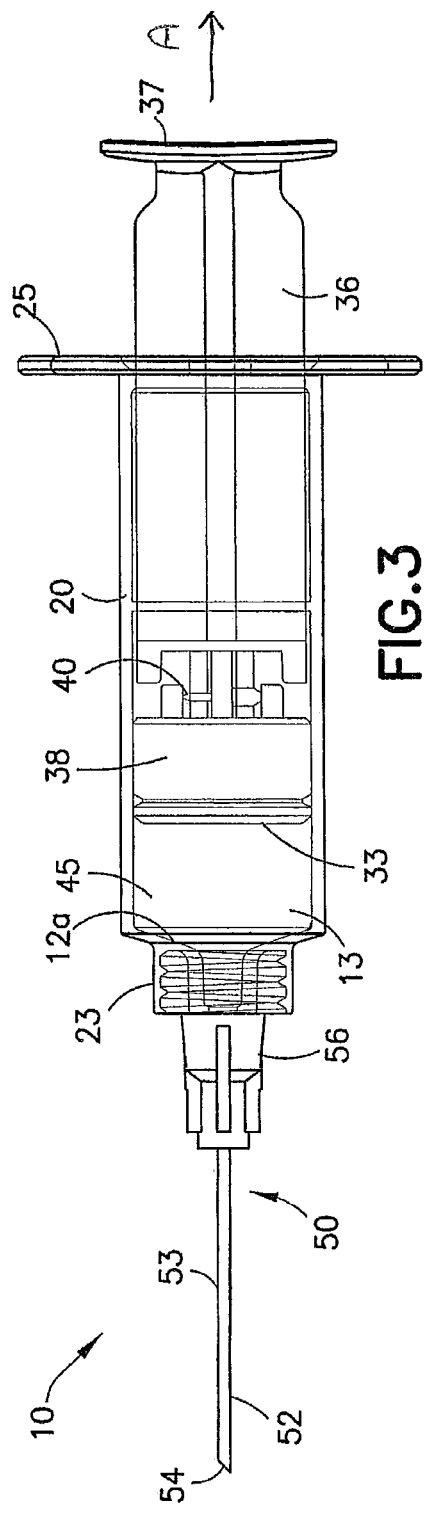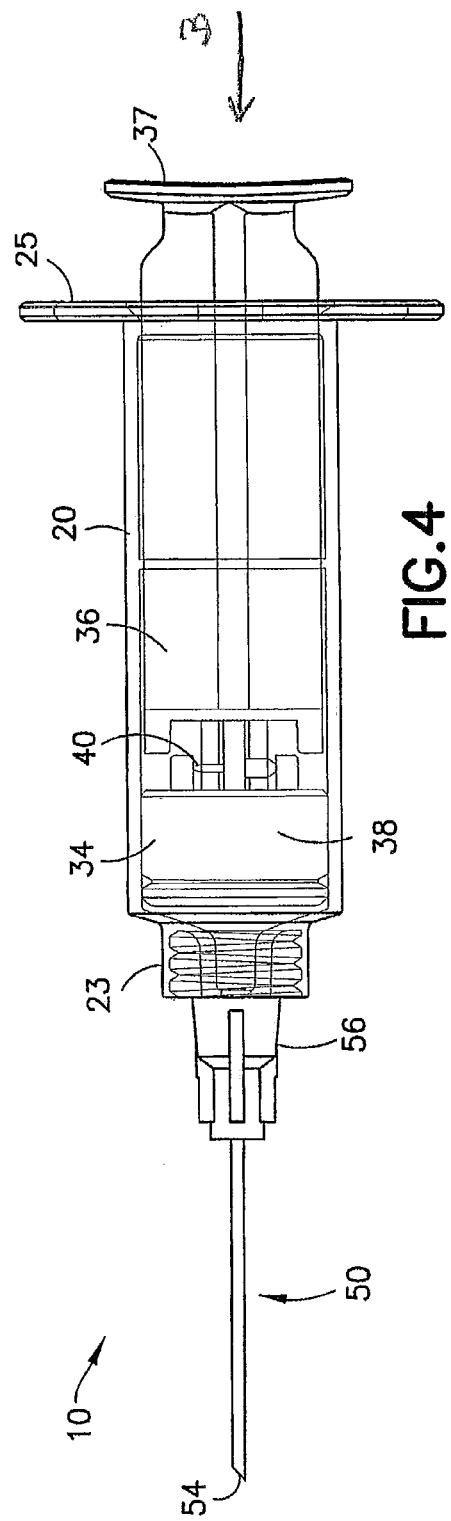

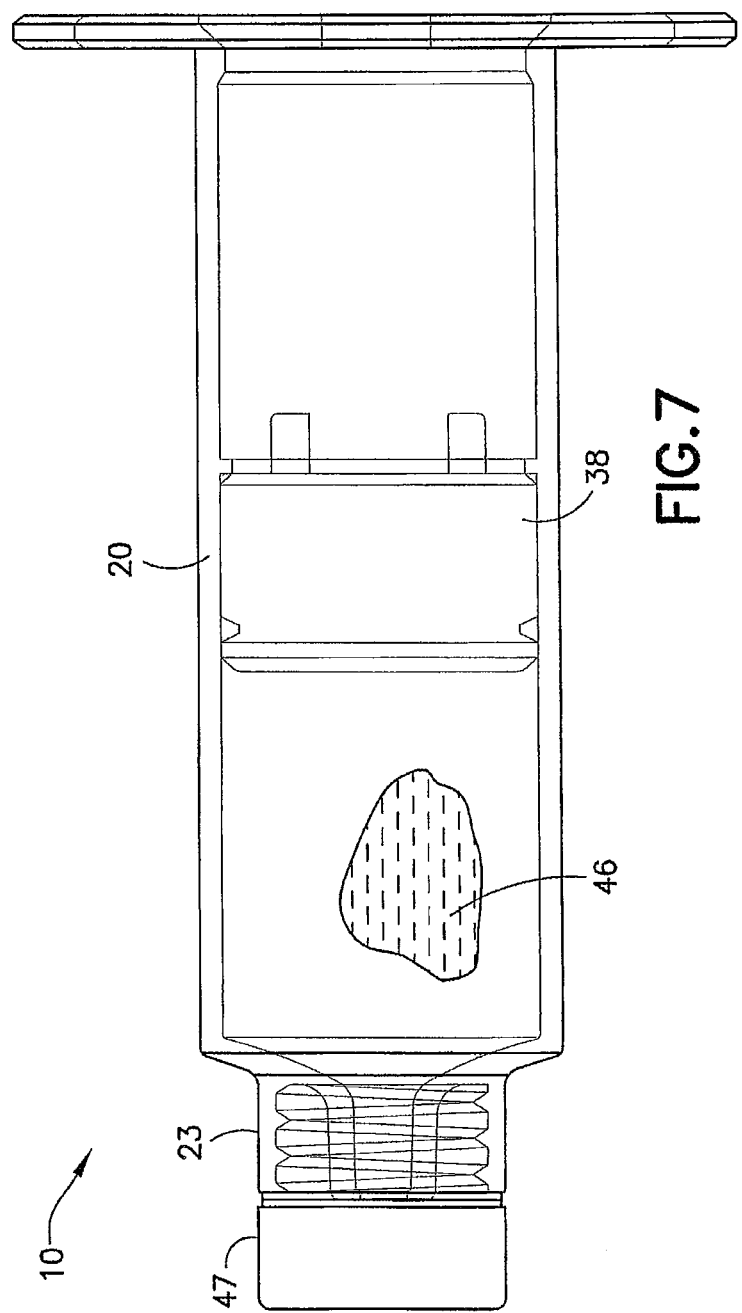

SYRINGE WITH BREAKABLE PLUNGER FOR ARTERIAL BLOOD GAS SAMPLE COLLECTION

CROSS-REFERENCE TO RELATED APPLICATIONS

This application is the United States national phase of International Application No. PCT/US2012/060790 filed Oct. 18, 2012, and claims priority to U.S. Provisional Patent Application No. 61/549,550 filed Oct. 20, 2011, the disclosures of which are hereby incorporated in their entirety by reference.

BACKGROUND OF THE INVENTION

Field of the Invention

The present invention is directed to a fluid collection assembly and methods for use thereof and more particularly, to a fluid collection assembly including a breakable plunger rod for use in arterial blood collection. The present invention is also directed to a fluid collection assembly configured for containing an anti-coagulant for the immediate association with a fluid sample upon collection of the sample.

Description of Related Art

Arterial blood collection syringes are used for withdrawing and collecting arterial blood samples from the body of a patient. Once the blood sample is collected, it is subjected to diagnostic analysis for gases, electrolytes, metabolites, and other elements that are indicative of a condition of a patient. Various types of syringes have been devised for collecting arterial blood samples, which mainly comprise elements from a hypodermic syringe, i.e., a plastic or glass syringe barrel, a sealing elastomeric stopper, and a plunger rod. Additionally, certain arterial blood collection syringes include a self-sealing filter that allows passage of air out of the syringe during blood collection, while still preventing the passage of blood. This latter type of syringe having a filter allows for an arterial sample to be collected without the need to aspirate the syringe, as is required with a syringe having a plunger rod and a plunger stopper.

Typical arterial blood collection syringes include a two-piece plunger rod assembly comprised of an elastomeric sealing stopper attached to a plunger rod. U.S. Pat. No. 5,314,416 to Lewis et al. discloses a low friction syringe assembly having a typical two-piece plunger rod and a plunger tip assembly. The sealing stopper and plunger rod must be assembled together in a separate operation prior to assembly with a syringe barrel. In addition, a silicone lubricant is usually used on the interior wall of the syringe barrel to facilitate easy slidable movement of the elastomeric sealing stopper against the interior wall of the syringe barrel. Such syringes typically involve an active step for obtaining a blood sample. For example, a needle connected to such a syringe accesses a patient's blood vessel, and the syringe is thereafter aspirated by the user holding the syringe with one hand and drawing the plunger rearwardly within the syringe barrel with the other hand so as to draw a blood sample into the syringe barrel for analysis. The need for the user to use two hands during the blood sample collection introduces unnecessary movement during the blood draw process and might cause discomfort to the patient.

Arterial blood samples can also be obtained passively through the use of a syringe having a plunger with a porous filter to collect blood by way of the blood pressure of a patient from whom the blood is being collected. In such a syringe, the plunger mechanism is typically hollow, and includes a porous filter therein. A separate elastomeric sealing stopper is typically attached to the front end of the plunger mechanism for sealing within the syringe barrel, with air channels in the stopper for air passage through the filter. In use, the plunger is set at a certain position against a graduated scale of the syringe barrel, so that the desired volume of the sample to be collected is represented by the cavity within the syringe. Once a blood vessel of a patient is accessed by an appropriate needle attached to the syringe, arterial blood will fill the syringe under its own pressure. As the cavity within the syringe fills, air within the syringe is allowed to escape from the syringe by way of a gas permeable filter. When the blood sample contacts the filter, the filter seals, thereby preventing escape of blood and ingress of air and other contaminants into the collected sample. U.S. Pat. No. 4,821,738 to Iwasaki et al. discloses an arterial blood gas syringe including a typical two-piece assembly for use. The arterial blood gas syringe is comprised of a plunger rod and an elastomeric sealing plug having channels formed in an upper surface for use in removing air as arterial blood is received in the syringe. The channels extend in a generally radial direction and converge near the center of a sealing plug to allow the passage of air to and through a filter element contained within the sealing plug. U.S. Pat. Nos. 5,377,689 and 5,529,738, both to Mercereau, disclose a sampling syringe including a plunger cap having an air permeable filter attached to a plunger rod, which is in slidable communication with the inner wall of a syringe barrel. However, the arterial blood collected using this type of syringe is exposed to air within the barrel interior of the syringe during the blood collection. This can affect the accuracy of the arterial blood gas analysis since oxygen and carbon dioxide can migrate into or out of the arterial blood sample depending on the partial pressure of gases in the arterial blood relative to atmospheric air.

After completion of the blood sample collection, the needle is removed and the syringe containing the collected blood sample is then transported to the laboratory. Typically blood samples collected in blood collection tubes are transported through pneumatic tubes between the ward and laboratory. However, the plunger that is protruding from the syringe barrel makes handling and transportation of the syringe difficult and special care has to be taken not to dislodge the plunger thus preventing pneumatic tube transportation and increasing the time and resources required to transport and analyze the collected blood sample.

Attempts have been made to prevent the re-use of syringes by providing breakable plunger rods as part of the syringe assembly, examples of which being disclosed in U.S. Pat. No. 6,217,550 (Capes), the entire content of which is incorporated herein by reference and in U.S. Patent Publication Number US 2006/0178625 (Lim et al.), the entire content of which is also incorporated herein by reference. Such breakable plunger rod assemblies provide a breakable connection between the main body of the plunger rod and the proximal distal portion. Such breakable connections possess sufficient structural integrity to resist breakage during normal use, but break upon application of additional force. Thus, after injection of the liquid contents of the syringe into a patient or into a suitable container or device such as through the pierceable septum of a catheter connector, a user applies additional force on the thumb press of the plunger rod. This additional force causes the breakable connection to shear, mechanically disconnecting the main body of the plunger rod from the distal portion, and hence disabling further use of the syringe.

It would therefore be desirable to provide an arterial blood collection syringe or assembly and method of use thereof which enables a single-handed blood collection technique, which does not expose the collected blood to atmospheric air prior to analysis for blood gas levels and allows the plunger to be removed to facilitate easier handling and transportation of the collected sample.

SUMMARY OF THE INVENTION

According to a first aspect, the invention is directed to a fluid collection assembly having a barrel having a proximal end, a distal end, and a sidewall extending between the proximal end and the distal end. The sidewall includes an internal surface defining an internal chamber. The fluid collection assembly also includes a stopper disposed within the barrel, a plunger rod having a proximal portion and a distal portion associated with the stopper, and a breakable connector joining the proximal portion and the distal portion of the plunger rod. The connector is adapted to break upon application of a breaking force to the plunger rod. An annular flange is provided that extends from the internal surface into the chamber which is configured to limit proximal movement of the stopper. The internal surface of the barrel is configured for slidably receiving the stopper in fluid tight engagement therewith.

The proximal end of the barrel, at least a portion of the internal surface of the sidewall, and the stopper define an internal reservoir configured for holding at least one of a fluid treatment additive, such as anticoagulants, clotting agents, stabilization additives, and the like and a fluid sample, such as arterial blood. The proximal end of the barrel includes structure for cooperating with a medical device. One example of a medical device that can be used with the fluid collection assembly can be a needle assembly having a lumen and wherein prior to collection of a fluid sample, the plunger rod is configured to prime the lumen and the internal reservoir with the fluid treatment additive and to remove any atmospheric air therefrom. The stopper has a distal face which can be configured to cooperate with an internal proximal surface of the barrel to minimize an amount of dead space within the reservoir. The proximal portion of the plunger rod can include a thumb flange and the stopper can be a low resistance stopper. The assembly can further include a tip cap configured to cooperate with the distal end of the barrel.

After the lumen and the internal reservoir are primed and the collection assembly is ready for use, an application of a breaking force is applied to the plunger rod to disconnect the proximal portion of the plunger rod from the connector and from the distal end of the plunger rod. The proximal portion of the plunger rod is then removed from the assembly. Upon collection of a fluid sample, such as upon insertion of the needle cannula in a patient's artery, the force of the blood filling the reservoir causes the stopper and distal end of the plunger rod to move in the proximal direction during collection. The annular flange extending from the internal sidewall of the barrel is configured to limit proximal movement of the stopper after application of this breaking force to the plunger rod and during the collection of a fluid or blood sample. The tip cap can be applied to the distal end of the barrel to prevent any spillage of the fluid sample during handling, storage, and transportation.

Generally, the present invention is directed to a method of collecting an arterial blood sample including the steps of providing a collection assembly, priming the collection assembly with a liquid anticoagulant, activating the breakable connection, and collecting a blood sample, wherein the arterial pressure during blood collection causes the stopper and the distal portion of the plunger rod to travel in a proximal direction along the barrel. Specifically, the invention is directed to a method of collecting a fluid sample including providing a fluid collection assembly having a barrel having a proximal end, a distal end, and a sidewall extending between the proximal end and the distal end, wherein the sidewall includes an internal surface defining an internal chamber, and a distal tip extending from the distal end having a passageway therethrough in fluid communication with the internal chamber. The fluid collection assembly also includes a stopper disposed within the barrel, a plunger rod having a proximal portion and a distal portion associated with the stopper, and a breakable connector joining the proximal portion and the distal portion of the plunger rod, wherein the connector is adapted to break upon application of a breaking force to the plunger rod. According to one embodiment, a needle assembly can be attached to the distal tip of said barrel. The method further includes priming the fluid collection assembly with a fluid treatment additive, breaking the breakable connector, and introducing the fluid sample into the internal chamber. The fluid sample can be a blood sample, such as arterial blood and the treatment additive can be any known blood treatment material such as an anticoagulant, a clotting agent, a stabilization additive, and the like. According to one embodiment, the fluid treatment additive can be in liquid form and can be an anticoagulant.

According to one embodiment, the proximal end of the barrel, at least a portion of the internal surface of the sidewall, and the stopper can define an internal reservoir. The step of priming the fluid collection assembly further comprises drawing a liquid anticoagulant into the internal reservoir and expelling air from the internal reservoir, the passageway, and a lumen of the needle assembly. The step of breaking the breakable connector includes exerting a force in a distal direction on the plunger rod a sufficient amount to cause the proximal portion to mechanically disconnect from the distal portion, and removing the proximal portion from the blood collection assembly.

The step of introducing the fluid sample can include inserting a distal end of the needle assembly into a source, such as a patient's artery, to cause fluid or blood to flow into the internal reservoir wherein the force of the fluid flow causes the stopper and the distal portion of the plunger rod to travel through the internal chamber toward the proximal end of the barrel until the stopper and the distal portion of the plunger rod contact an annular flange extending inwardly from the internal surface of the barrel sidewall and into the internal chamber of the barrel. After completion of fluid collection, the method further includes removing the distal end of the needle assembly from the fluid source or patient, removing the needle assembly from the distal tip of the barrel, and attaching a tip cap to the distal tip of the barrel to prevent any spillage of the fluid sample during handling, storage, and transportation.

BRIEF DESCRIPTION OF THE DRAWINGS

FIG. 3 is a schematic partially cross-sectional side view of the fluid collection assembly as shown in FIG. 1 during the drawing of liquid anticoagulant into the fluid collection assembly in accordance with an embodiment of the present invention.

FIG. 4 is a schematic partially cross-sectional side view of the fluid collection assembly as shown in FIG. 1 during the activation of the breakable connection in accordance with an embodiment of the present invention.

FIG. 7 is a schematic partially cross-sectional side view of the fluid collection assembly as shown in FIG. 1 when prepared for transportation and testing in accordance with an embodiment of the present invention showing a portion of the sidewall removed.

DETAILED DESCRIPTION OF THE INVENTION

Figure 1:
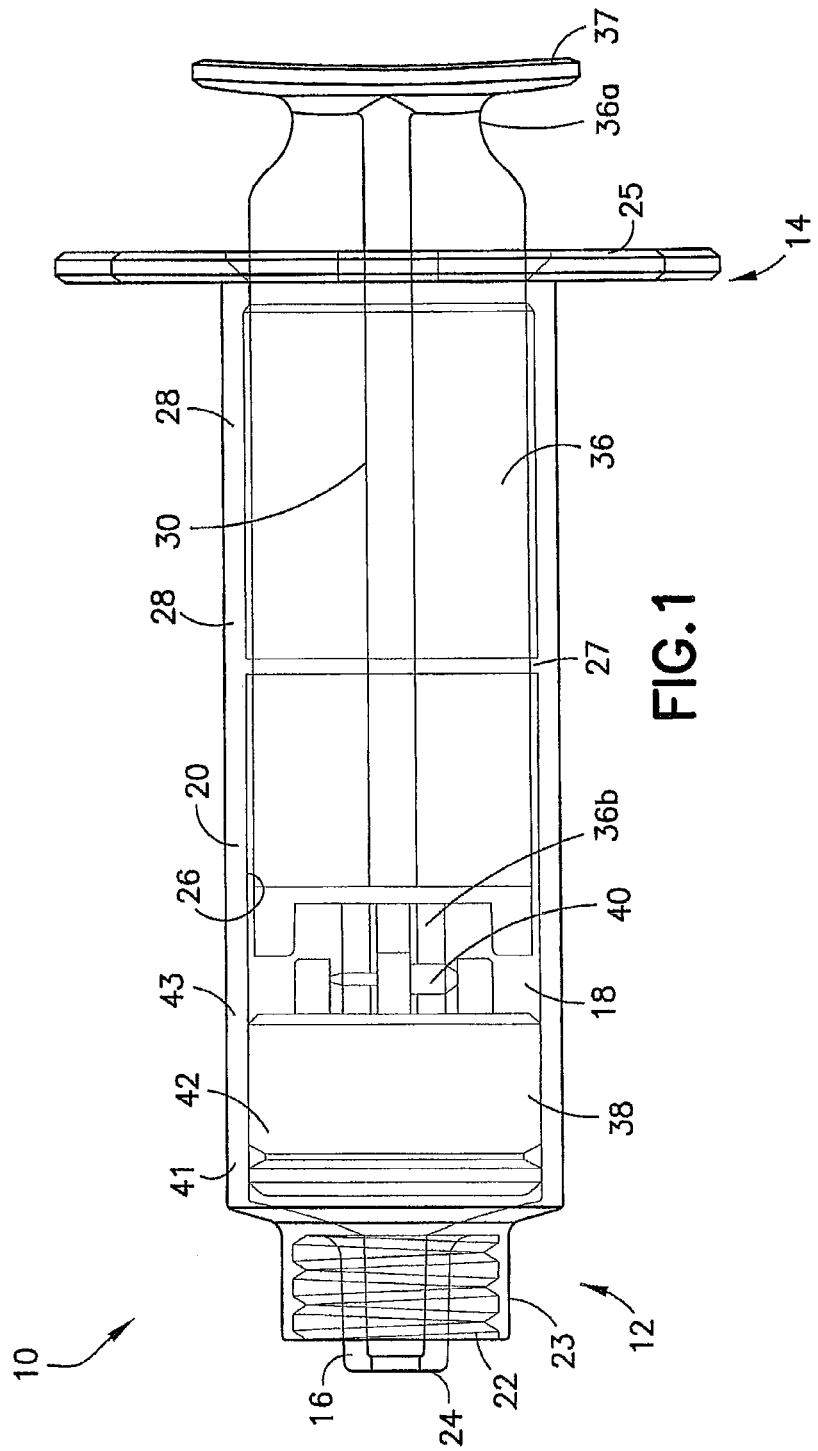
FIG. 1 is a schematic partially cross-sectional side view of a fluid collection assembly in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used herein, the term "proximal" refers to a location on the blood collection assembly according to the embodiments of this invention that, during normal use, is closest to the clinician using the device and farthest from the patient in connection with whom the device is used. Conversely, the term "distal" refers to a location on the blood collection assembly of this invention that, during normal use, is farthest from the clinician using the device and closest to the patient in connection with whom the device is used. Furthermore, the term "proximal direction" indicates a direction of movement away from the patient and toward the user of the blood collection assembly, whereas the term "distal direction" indicates a direction of movement away from the user of the blood collection assembly and toward the patient.

Referring to the drawings in which like reference characters refer to like parts throughout the several views thereof, FIGS. 1-7 illustrate a fluid collection assembly, generally illustrated as 10. According to one embodiment, the fluid collection assembly 10 can comprise an arterial blood collection assembly and thus, the present invention is generally described in terms of an arterial blood collection assembly. The fluid collection assembly includes a plunger rod 30 in slidable communication with a barrel 20 having a standard luer fitting 23 at a distal end 12 for connection to an arterial access device, such as a needle assembly, generally indicated as 50. While described herein in terms of an arterial blood collection assembly 10 intended for use with a needle assembly 50, the assembly 10 of the present invention may be used with or may incorporate other medical devices, such as another medical device assembly that includes a piercing element or allows for attachment to a catheter.

Figure 2:
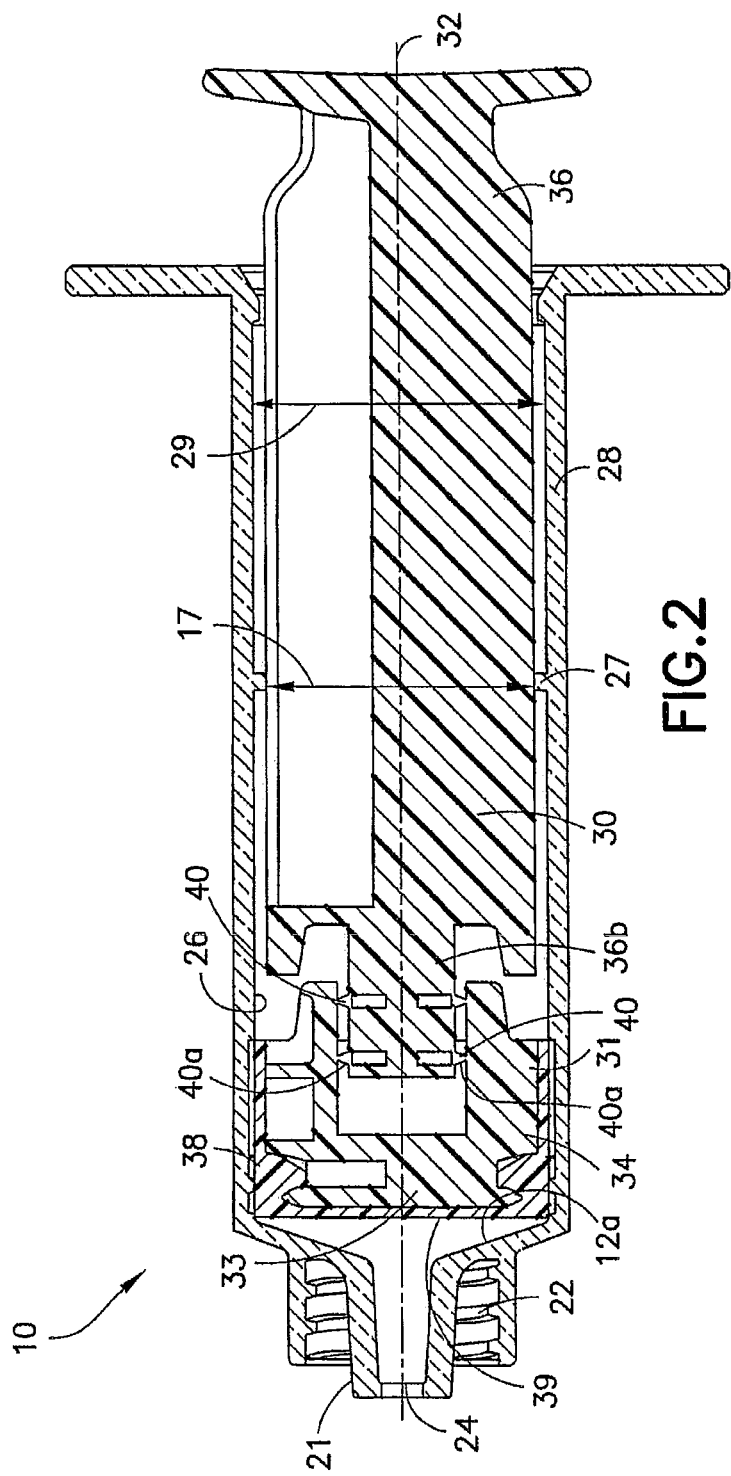
FIG. 2 is a schematic cross-sectional side view of the fluid collection assembly as shown in FIG. 1 in accordance with an embodiment of the present invention.

With continuing reference to FIGS. 1 and 2, the fluid collection assembly 10 includes a barrel 20, which can be an elongated, hollow, cylindrically-shaped tube having an open proximal end 14, a generally closed distal end 12, and a rigid tubular sidewall 28 extending between the proximal end 14 and the distal end 12. The sidewall 28 includes an internal surface 26 defining an internal chamber 18.

Barrel 20 may be made of one or more than one of the following representative materials: polypropylene, polyethylene, polyethyleneterephthalate (PET), polystyrene, polycarbonate, cellulosics, glass products, or combinations thereof. More expensive plastics such as polytetrafluoroethylene and other fluorinated polymers may also be used. In addition to the materials mentioned above, examples of other suitable materials include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF, and perfluoroalkoxy resins. One exemplary glass product is PYREX® (available from Corning Glass, Corning, N.Y.). Ceramic collection devices can be used according to embodiments of the invention. Cellulosic products such as paper and reinforced paper containers can also be used to form collection devices according to the invention.

Referring back to FIGS. 1 and 2, the fluid collection assembly also includes a stopper 38 located within the barrel 20, a plunger rod 30 having a proximal portion 36 and a distal portion 34 associated with the stopper 38, and a connector 40 joining the proximal portion 36 and the distal portion 34 of the plunger rod 30. The connector 40 is adapted to break or collapse upon application of a breaking force to the plunger rod 30. The internal surface 26 of the barrel 20 is configured for slidably receiving the stopper 38 in fluid tight engagement therewith and for receiving the breakable or collapsible plunger rod 30. The stopper 38 is slidably positioned in fluid tight engagement with the internal surface 26, and is able to slide distally and proximally along a longitudinal axis 32. According to one embodiment, the stopper 38 may be a separate element connected to the distal portion 34 of the plunger rod 30. Alternatively, the stopper 38 may be integrally molded with the distal portion 34 in a one-piece plastic construction.

According to an embodiment of the invention as shown in FIGS. 2 and 3, stopper 38 encloses a portion of an external surface 31 and a distal face 33 of distal portion 34. Stopper 38 may be separately attached to distal portion 34, or may be integrally molded over the external surface 31 and distal face 33 of distal portion 34 of plunger rod 30. The diameter of stopper 38 is approximately equal to or only slightly bigger or smaller than that of an internal diameter 29 of the barrel 20 but is greater than an internal diameter 17 of an annular flange 27. Stopper 38 is in slidable contact with internal surface 26 of barrel 20 and provides a fluid-tight seal between the plunger rod 30 and the internal surface 26 of the barrel 20 so that a sample can be held within an internal reservoir 13 formed within the chamber 18 between distal end 12 of barrel 20 and distal face 33 of plunger rod 30, thereby preventing the sample from leaking from assembly 10.

Figure 6:
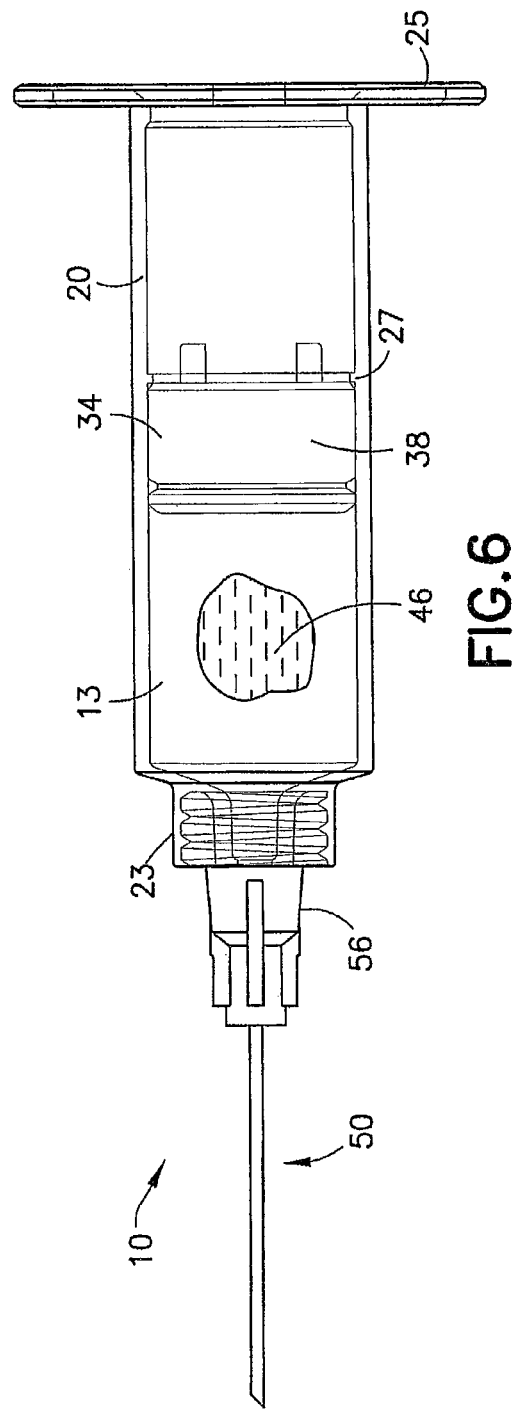
FIG. 6 is a schematic partially cross-sectional side view of the fluid collection assembly as shown in FIG. 1 upon completion of collection of a fluid sample in accordance with an embodiment of the present invention showing a portion of the sidewall removed.

With reference to FIG. 6, according to one embodiment, stopper 38 can be a low resistance stopper and as such is designed to have a relatively lower frictional resistance to movement inside of barrel 20 when compared to similar components in prior art arterial blood gas syringes such that the presence of arterial blood pressure within internal reservoir 13 will cause the distal portion 34 to slide/travel in a proximal direction toward the proximal end 14 of barrel 20 until the distal portion contacts annular flange 27 thereby limiting the proximal movement of distal portion 34. The frictional resistance of a stopper can be lowered by either the stopper sealing profile design and/or the component material selection. In the embodiment shown in FIG. 1, first and second sealing rings 41, 42 extend around the outer circumferential surface of stopper 38 near to distal face 33 to create a primary and secondary seal with internal surface 26 of barrel 20. A third sealing ring 43 can be provided which forms a third seal and assists in the stabilization of the distal portion 34, thereby centralizing the plunger rod 30 during slidable movement of the plunger rod 30 relative to the barrel 20. This stopper sealing profile design lowers the amount of contact between stopper 38 and internal surface 26 thereby reducing the frictional resistance to movement of stopper 38 when compared to a stopper sealing profile in which the entire outer circumferential surface is in contact with internal surface 26. Alternately or in combination with the stopper sealing profile design, stopper 38 is preferably made of an elastomeric material such as natural rubber, synthetic rubber, thermoplastic elastomers and combinations thereof which are formulated or synthesized to be self-lubricating or have relatively lower frictional resistance. Stopper 38 may also be made from a combination of elastomers which include a harder inner rubber core and a soft "Epilor" outer layer.

Plunger rod 30 can be constructed of a suitable polymeric material, and may be manufactured by injection molding with a suitable polymer material known in the art. It is within the purview of the present invention to include plunger rods and stoppers which are separately formed or integrally formed of the same material or different materials such as in two-color molding, or separately formed of the same or different materials and joined together by mechanical means, adhesives, ultrasonic welding, heat sealing or other suitable means.

The breakable/collapsible connector 40 is strong enough to hold the proximal portion 36 and the distal portion 34 of the plunger rod 30 together during normal use of the fluid collection assembly 10 and is breakable upon application of a breaking force to the proximal portion 36 of the plunger rod 30. In particular, the breakable connection 40 is manufactured to withstand typical-use shear forces generated when a user draws fluids into the fluid passageway, or expels them through an opening 24 during normal use in medical procedures. However, upon the application of a certain breaking force indicated by arrow B in FIG. 4, the breakable connection 40 activates and breaks. The breaking force should not be so small as to risk unintentional activation of breakable connection 40 during application of force during normal use or during assembly of the assembly 10, nor too great as to place undue strain on the user. Accordingly, when a user presses down upon a thumb flange 37 with the intent to disable the syringe function of the arterial blood collection assembly 10, proximal portion 36 mechanically disconnects from distal portion 34. Thus, the breaking force is the total force that includes the force applied under normal use plus some additional force required to break the breakable connection. Useful breakable or collapsible plunger rods are found, for example, in U.S. Pat. Nos. 6,217,550; 7,798,993; and U.S. Patent Publication Nos. US 2006/0195063 and US 2004/0064105 the contents of which are hereby incorporated by reference in their entirety.

The breaking force depends on various dimensions of the syringe barrel 20 and plunger rod 30, the viscosity of the liquid being delivered and the mechanical and hydraulic forces encountered by the filling and delivery process. If the breakable connection 40 is too weak, the proximal portion 36 and distal portion 34 will separate during assembly or normal use of the collection assembly 10, and if the force required to break the breakable connection 40 is too high the user may not be able to easily break the breakable connection 40 as intended. The skilled artisan can select the appropriate materials and/or connections to provide the proper breaking force to cause the connection to break and the plunger rod 30 to collapse for a particular collection assembly design and/or use.

With particular reference to FIG. 2, a plurality of breakable connections 40 can be provided connecting the proximal portion 36 and the distal portion 34 of the plunger rod 30. These connections 40 may connect the proximal portion 36 of the plunger rod 30 and the distal portion 34 of the plunger rod 30 at a breakable connection point 40a. The connections 40 can be in the form of protuberances extending in a transverse direction with respect to a longitudinal axis of the plunger rod 30. Alternatively, the breakable connection 40 can be in the form of a circular shaped projection or protuberance which is configured to fit into a cylindrically shaped recess in the distal portion 34 of the plunger rod 30.

With continuing reference to FIG. 2, according to one embodiment, the connection 40 may be molded integrally with the proximal portion 36 and the distal portion 34 of the plunger rod 30. A wide variety of plastic materials are suitable for molding the plunger rod 30 including polystyrene, polypropylene, and polyethylene. When molding, the modulus of elasticity of the material selected to form the connection 40 must be controlled to ensure that the breakable connection breaks or fails before the proximal portion 36 bottoms out or makes contact with the distal portion 34 of the plunger rod 30. If the modulus is too high, the break will occur too easily, causing premature breakage. If the modulus is too low, the breakable connection may not break before the proximal portion and the distal portion contact each other. According to one embodiment, it is desirable to have a modulus of elasticity within the range of about 800 MPa to 4000 MPa.

The breakable connection point 40a can be located anywhere along the protuberance of the connection 40 depending upon the geometry of the protuberance. As discussed above, the connection 40 can be integrally molded with the plunger rod. According to another embodiment, the connection 40 can be connected to one or both of the proximal portion 36 or the distal portion 34 with a frangible adhesive. The connection 40 can be very short and made entirely of adhesive or frangible material. According to yet another embodiment, the connection 40 can be made using a shear pin passing through the distal end 36b of the proximal portion 36 and through the distal portion 34 of the plunger rod 30. According to still another embodiment, the breakable connection 40 can be accomplished by using a snap-fit arrangement, a portion of which is damaged or broken when the desired force is applied. In this situation, the distal portion 34 and the proximal portion 36 can be individually molded and snapped together during the assembly process.

A proximal end 36a of the proximal portion 36 may include a thumb flange 37 that a user may push to move the plunger rod 30 and stopper 38 distally, or pull to move the plunger rod 30 and stopper 38 proximally in relation to barrel 20. By moving the plunger rod distally, the stopper 38 may force fluids out of the fluid passage way through opening 24 in the distal tip 16. By moving proximally, the stopper 38 may draw fluids through the fluid passageway and into chamber 18. The flange 37 also facilitates the application of a force to the plunger rod 30 to break the breakable connection 40, such as by the application of a distal force thereto, as described in further detail below. An external flange 25 can also be provided at the proximal end 14 of the barrel 20 to facilitate handling of the fluid collection assembly 10 and for applying forces to the plunger rod 30 using a one-handed procedure.

An annular flange 27 is provided that extends from the internal surface 26 into the chamber 18 which is configured to limit proximal movement of the stopper 38 and the distal portion 34 of the plunger rod 30. The internal surface 26 of the barrel 20 is configured for slidably receiving the stopper 38 in fluid tight engagement therewith. The annular flange 27 has a diameter 17 that is less than diameter 29 of the barrel 20.

Figure 5:
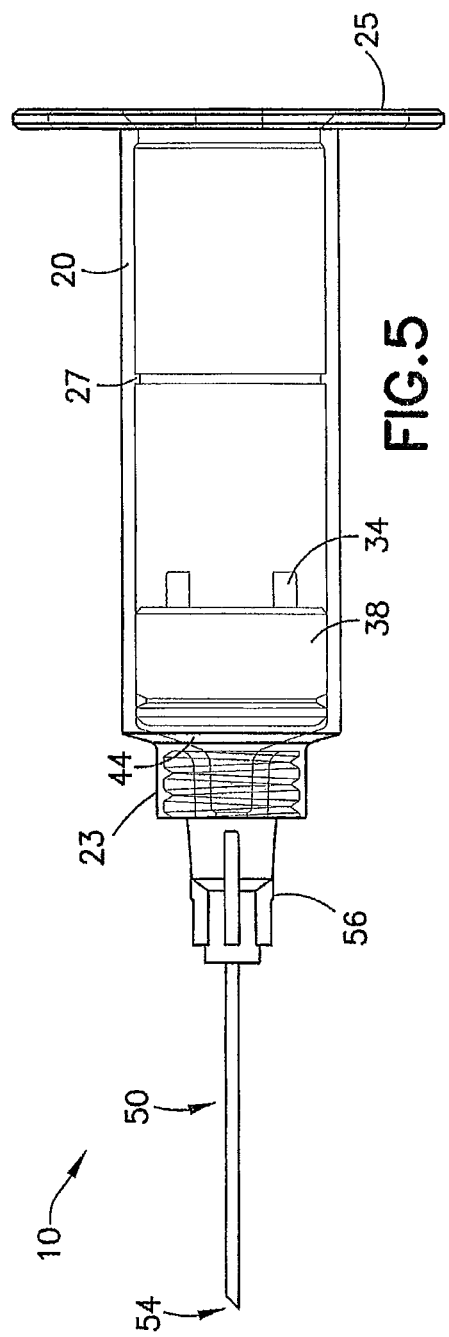
FIG. 5 is a schematic partially cross-sectional side view of the fluid collection assembly as shown in FIG. 1 after activation of the breakable connection and prior to collection of a blood sample in accordance with an embodiment of the present invention.
Figure 5A:
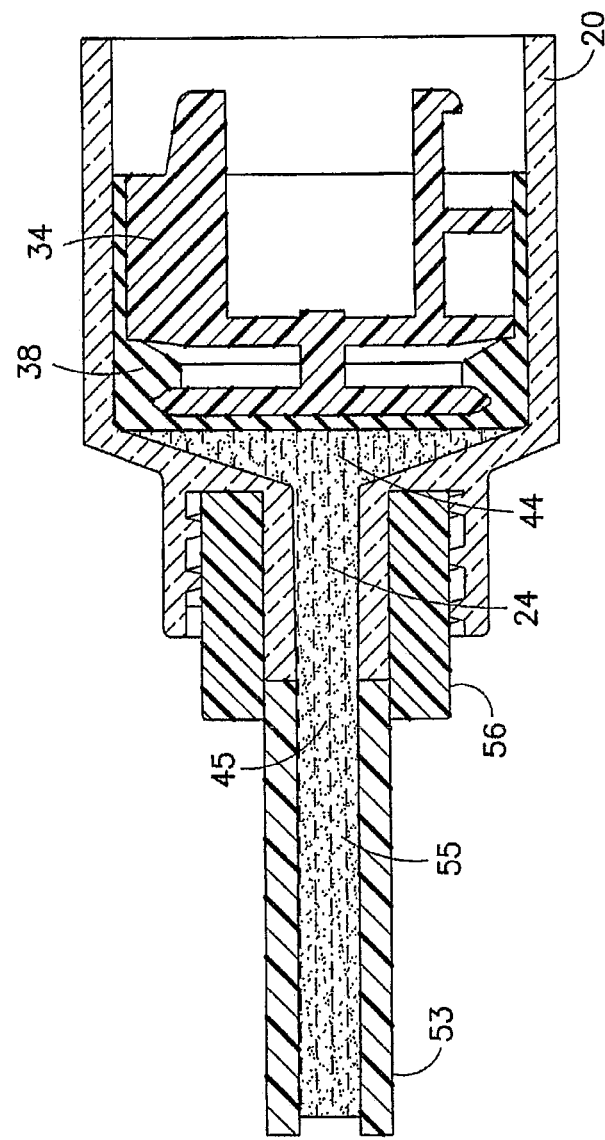
FIG. 5A is a schematic partially cross-sectional enlarged partial view of the distal end of the plunger rod of the fluid collection assembly as shown in FIG. 5 in accordance with an embodiment of the present invention.

The proximal end 14 of the barrel 20, at least a portion of the internal surface 26 of the sidewall 28, and a distal face 39 of the stopper 38 define an internal reservoir 13 configured for holding at least one of fluid treatment additive 45, as shown in FIG. 5A, as required for particular testing procedures, such as anticoagulants, clotting agents, stabilization additives, and the like and a fluid sample, such as arterial blood. The anticoagulants may include hirudins, hirudin derivatives, chelating agents, or chelating agent derivatives. Specific anticoagulants include citrate, ethylenediaminetetraacetic acid (EDTA), heparin, CPAD, CTAD, CPDA-1, CP2D, potassium oxalate, sodium fluoride, or ACD. The anticoagulant used is liquid in form to improve the incorporation hence effectiveness of the anticoagulant upon collection of arterial blood. The liquid form can be an emulsion, solution, or dispersion of the anticoagulant in a suitable carrier. Typically prior art arterial blood sample collection methods use an arterial blood gas syringe pre-loaded upon manufacture with a solid form of anticoagulant such as heparin powder within the syringe barrel in order to maximize the shelf life of the syringe. The use of a solid form of anticoagulant can cause a reduction in the effectiveness of the anticoagulant as the incorporation of powdered heparin into the blood sample is difficult due to lack of agitation during the arterial blood collection process. The clotting agent may be kaolin or thrombin or silica based. Such additives may be in particle or liquid form and may be sprayed onto the internal surface 26 of the barrel 20 or located within fluid reservoir 13.

With particular reference to FIGS. 2-6, the proximal end 14 of the band 20 includes structure for cooperating with a medical device. It will be appreciated by those skilled in the art that distal tip 16 of the blood collection assembly 10 may be releasably or permanently connected to the needle assembly 50 via a hub fitting 56 as is known in the art. Such needle assemblies include, but are not limited to, luer lock type needle assemblies and luer slip type needle assemblies. For example, a standard luer fitting including a male luer taper 21 and an internally threaded luer lock 22 may be provided at the distal end 12 of barrel 20, as shown in FIG. 2, for removably receiving a corresponding fitting of an arterial access device. More particularly, an arterial access device such as a needle assembly 50 as shown in FIGS. 3-6 may include a needle cannula 53 having a proximal end and a distal end 52 and an interior lumen 55 extending therebetween as shown in FIG. 5A. The distal end 52 defines a needle cannula 53 beveled at the distal end 52 to define a sharp puncture tip 54 for intravenous puncture into the blood vessel of a patient, such as an artery. Puncture tip 54 is designed to provide ease in insertion and minimal discomfort for the patient during arterial access. The proximal end 51 of needle assembly 50 is contained within the hub fitting 56. The hub fitting 56 includes an internal female luer taper and a pair of opposing flanges. In this manner, needle assembly 50 can be releasably attached to the distal end 12 of barrel 20 by the corresponding interfitting engagement between male luer taper 21 and female luer taper of the hub fitting 56, as well as through the locking engagement between luer flanges and luer lock 22, as is well known in the art. As such, fluid communication can be established between the interior lumen 55 of needle cannula 53 and chamber 18 of collection assembly 10.

Assembly of the arterial blood collection assembly 10 is accomplished by slidably inserting plunger rod 30 within chamber 18 through proximal end 14 of barrel 20. Breakable connection 40 has sufficient strength such that stopper 38 can be forced through annular flange 27 without the activation thereof. The assembly can then be packaged for later use. When assembled as such, fluid communication is generally established throughout the length of the assembled arterial blood collection assembly 10. Specifically, fluid communication is provided through opening 24 at the front or distal end of barrel 20 (and likewise through needle cannula 53 attached thereto), into chamber 18, and more particularly the fluid reservoir 13, in barrel 20.

In use, the fluid collection assembly 10, according to an embodiment of the invention, is attached to needle assembly 50. Prior to collection of a fluid sample, the plunger rod 30 is configured to prime the lumen 55 and the internal reservoir 13 with the fluid treatment additive 45, as shown in FIG. 5A, and to remove any atmospheric air therefrom. The stopper 38 has a distal face 39 which can be configured to cooperate with an internal proximal surface 12a, as shown in FIG. 2, of the barrel 20 to minimize an amount of dead space within the reservoir 13. After the lumen 55 and the reservoir 13 are primed and the collection assembly 10 is ready for use, an application of breaking force is applied to the plunger rod 30 to disconnect the proximal portion 36 of the plunger rod 30 from the connector 40 and from the distal end 34 of the plunger rod 30. The proximal portion 36 of the plunger rod 30 is then removed from the fluid collection assembly 10. Upon collection of a fluid sample, such as upon insertion of the needle cannula 53 in a patient's artery, the force of the blood 46, as shown in FIGS. 6 and 7, filling the reservoir 13 causes the stopper 38 and distal portion 34 of the plunger rod 30 to move in the proximal direction during collection. The annular flange 27 extending from the internal surface 26 of the sidewall 28 of the barrel 20 is configured to limit proximal movement of the stopper 38 after application of this breaking force to the plunger rod 30 and during the collection of a fluid or blood sample.

According to one embodiment, the fluid collection assembly can be primed by drawing a liquid anticoagulant 45, such as heparin, from a vial, ampoule, or other suitable container using known safe procedures into fluid reservoir 13 of arterial blood collection assembly 10 by pulling the plunger rod 30 in a proximal direction indicated by arrow A as shown in FIG. 3. Air is then expelled from the fluid reservoir 13 and needle lumen by the standard techniques known in the art, e.g., holding the assembly 10 in a vertical orientation with the distal end 52 of needle cannula 53 in an upward direction and one's flicking fingers against the barrel wall 28, then pressing plunger rod 30 in a upward or distal direction to expel any air present.

According to embodiments of the invention, plunger rod 30 can be moved back and forth along the barrel 20 as many times as necessary to properly fill the barrel 20 without activation of breakable connection 40. For example, the barrel 20 may be filled with sterile water and then the sterile water can be injected into a vial containing a lyophilized medication which is then drawn back into the barrel 20. Many single-use syringes in the prior art only allow one proximal motion of the plunger with respect to the barrel. With these single-use syringes, once the plunger is moved in a distal direction with respect to the barrel it can no longer be withdrawn. Therefore, repeated distal and proximal movements of the plunger as described above are not possible.

A user then presses down upon thumb flange 37 with sufficient force in a distal direction until the breakable connection 40 activates and the proximal portion 36 mechanically disconnects from distal portion 34. The proximal portion 36 can then be separated from the distal portions as shown in FIGS. 4-5. With the residual liquid anticoagulant 45 present in a remaining dead space 44 within the fluid reservoir, the opening 24 in tip 16 and the lumen 55 of the needle 53 (as shown in FIG. 5A) should be at a concentration so as to provide sufficient anticoagulant function to prevent the clotting of the arterial blood sample upon collection. The assembly 10 is now primed with liquid heparin.

The purpose of priming assembly 10 with anticoagulant is to remove any atmospheric air, so that the partial pressure of the oxygen in the arterial blood sample will not be affected by the atmospheric air. The assembly 10 should preferably have low dead space to keep the residual volume of the heparin low in order to minimize the dilution effect of the liquid heparin on the blood sample.

Figure 9:
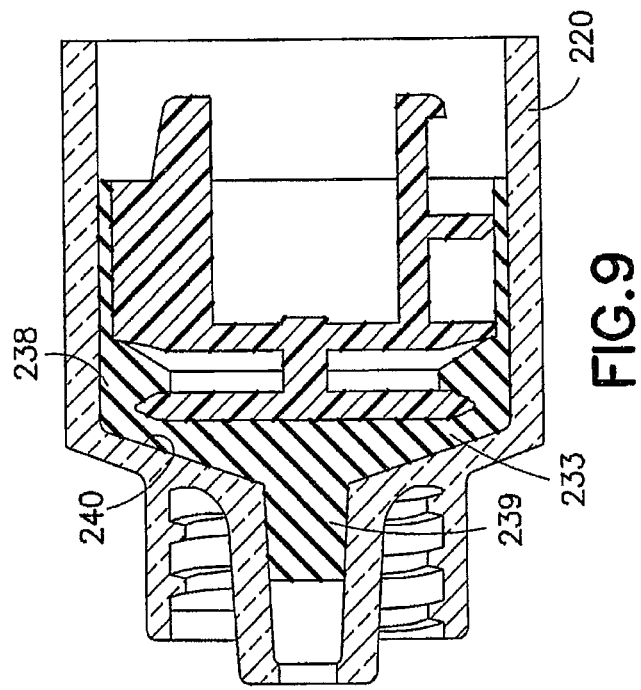
FIG. 9 is an enlarged partially cross-sectional side view of the distal end of the plunger rod of a fluid collection assembly in accordance with an embodiment of the present invention.
Figure 8:
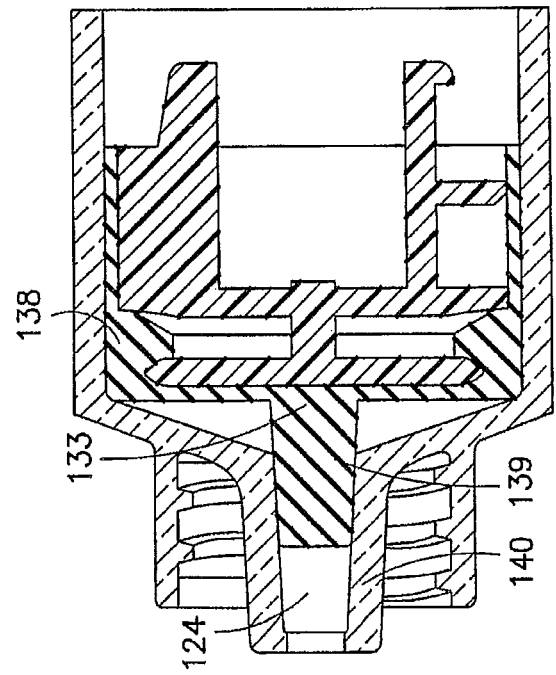
FIG. 8 is an enlarged partially cross-sectional side view of the distal end of the plunger rod of a fluid collection assembly in accordance with an embodiment of the present invention.

Reference is now made to FIGS. 8 and 9, which show two stopper profiles designed to reduce the amount of residual liquid anticoagulant present after activation of breakable connection 40. FIG. 8 shows a stopper 138 with a finger 139 extending in a distal direction from the center of a distal face 133. The shape of finger 139 is designed to mate with an inner surface 140 of a fluid pathway 124 in order to displace any liquid present in fluid passage 124 upon activation of breakable connection. FIG. 9 shows a stopper 238 with a distal face 233 having a conical profile 239 which is shaped to mate with a distal internal surface 240 of a barrel 220 thereby minimizing the dead space that could occur within the fluid reservoir.

As discussed above, the present invention is directed to a method of collecting an arterial blood sample including the steps of providing a collection assembly, priming the collection assembly with a liquid anticoagulant, activating the breakable connection, and collecting a blood sample wherein the arterial pressure during blood collection causes the distal portion of the plunger rod to travel in a proximal direction along the barrel.

A method of blood collection according to an embodiment of this invention enables a single-handed technique in the blood collection process using a low resistance rubber stopper that is moved by the arterial pressure. The user grips assembly 10 as shown in FIG. 5 with one hand and inserts puncture tip 54 into the artery. Blood at arterial pressure (which is greater than normal atmospheric or ambient pressure) will then flow through lumen 55, opening 24 in tip 16 and into the fluid reservoir 13, and forces stopper 38 to slide in proximal direction until the proximal face contacts flange 27 thereby defining the completion of the collection volume of the blood sample. The puncture tip 54 is then removed from the artery. The sliding motion of the rubber stopper 38 allows the liquid anticoagulant 45 and the collected arterial blood 46 to mix during the collection process, as shown in FIG. 6. Needle assembly 50 is then carefully replaced with a tip cap 47 that is compatible with luer connection as shown in FIG. 7 to prevent any spillage of the blood sample during handling, storage, and transportation. The blood collection assembly 10 containing the aseptic arterial blood sample as shown in FIG. 7 is then ready for transportation to the laboratory for Arterial Blood Gas analysis.

While the present invention is satisfied by embodiments in many different forms, there is shown in the drawings and described herein in detail the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A fluid collection assembly comprising:
   a barrel having a proximal end, a distal end, and a sidewall extending between the proximal end and the distal end, said sidewall including an internal surface defining an internal chamber;
   a stopper disposed within the barrel;
   a plunger rod having a proximal portion and a distal portion associated with the stopper;
   a breakable connector joining the proximal portion and the distal portion of the plunger rod, said connector adapted to break upon application of a distally directed breaking force to the plunger rod; and
   an annular flange extending from the internal surface into the chamber, said annular flange configured to limit proximal movement of the stopper.

2. The fluid collection assembly of claim 1, wherein the internal surface is configured for slidably receiving the stopper in fluid tight engagement therewith.

3. The fluid collection assembly of claim 1, wherein the proximal end of the barrel, at least a portion of the internal surface of the sidewall, and the stopper define an internal reservoir configured for holding at least one of a fluid treatment additive and a fluid sample.

4. The fluid collection assembly of claim 3, wherein the proximal end of the barrel includes structure for cooperating with a medical device.

5. The fluid collection assembly of claim 4, wherein the medical device comprises a needle assembly having a lumen and wherein prior to collection of a fluid sample, the plunger rod is configured to prime the lumen and the internal reservoir with the fluid treatment additive and to remove any atmospheric air therefrom.

6. The fluid collection assembly of claim 5, wherein the stopper has a distal face configured to cooperate with an internal proximal surface of the barrel to minimize an amount of dead space within the reservoir.

7. The fluid collection assembly of claim 1, wherein the annular flange is configured to limit proximal movement of the stopper after application of a breaking force to the plunger rod and during the collection of a fluid sample.

8. The fluid collection assembly of claim 1, wherein the proximal portion of the plunger rod includes a thumb flange.

9. The fluid collection assembly of claim 1, wherein the stopper is a low resistance stopper.

10. The fluid collection assembly of claim 1, including a tip cap configured to cooperate with the distal end of the barrel to prevent any spillage of a fluid sample during handling, storage, and transportation.

\* \* \* \* \*